United States Patent [19]

Wollnik et al.

[11] 4,445,516
[45] May 1, 1984

[54] PROCESS FOR THE DIGITIZATION AND DISPLAY OF THERMOGRAPHIC RECORDS

[75] Inventors: Hermann Wollnik, Fernwald; Rudiger Haas, Altenkirchen; Folkert Kassen, Lahnau-Atzbach, all of Fed. Rep. of Germany

[73] Assignee: Carl Zeiss-Stiftung, Oberkochen Wierttemberg, Fed. Rep. of Germany

[21] Appl. No.: 336,397
[22] PCT Filed: May 26, 1981
[86] PCT No.: PCT/DE81/00076
§ 371 Date: Dec. 18, 1981
§ 102(e) Date: Dec. 18, 1981
[87] PCT Pub. No.: WO81/03418
PCT Pub. Date: Dec. 10, 1981

[30] Foreign Application Priority Data

May 29, 1980 [DE] Fed. Rep. of Germany ....... 3020352

[51] Int. Cl.³ .............................................. A61B 5/00
[52] U.S. Cl. ...................................... 128/736; 364/415
[58] Field of Search ........................ 128/736, 399–403; 374/112–113, 124; 364/415

[56] References Cited

U.S. PATENT DOCUMENTS 3,699,813 10/1972 Lamb .................................. 128/736
3,970,074 7/1976 Mogos et al. ...................... 128/736
4,186,748 2/1980 Schlager .............................. 128/736
4,218,707 8/1980 Reed et al. ...................... 128/736 X
4,275,741 6/1981 Edrich ............................. 128/736 X

OTHER PUBLICATIONS

"Microprocessors Enhance Thermograms to Aid Diagnosis of Breast Tumors", *Electronics*; vol. 49, No. 14, 7-1976, p. 8E.

*Primary Examiner*—Lee S. Cohen
*Assistant Examiner*—Angela D. Sykes

[57] ABSTRACT

A method for digitizing and displaying thermographic records of biological or technical structures which makes it possible to recognize abnormal temperature distributions even if they are very small or the corresponding regions differ only very slightly in their temperature value from the adjacent temperature values. In this method, the temperature values at each image point of a thermogram are digitized and the slope of the local change in temperature, i.e. the temperature gradient, is calculated for each image point on basis of its temperature and the measured temperature values of its neighboring points. For a selected image region the local distribution of the temperature gradients is displayed. Abnormal temperature distributions can be recognized from this display at places where large temperature gradients are present.

The method is particularly advantageous for use in the field of medicine and serves there for the detection of carcinomas and particularly breast cancer.

10 Claims, 5 Drawing Figures

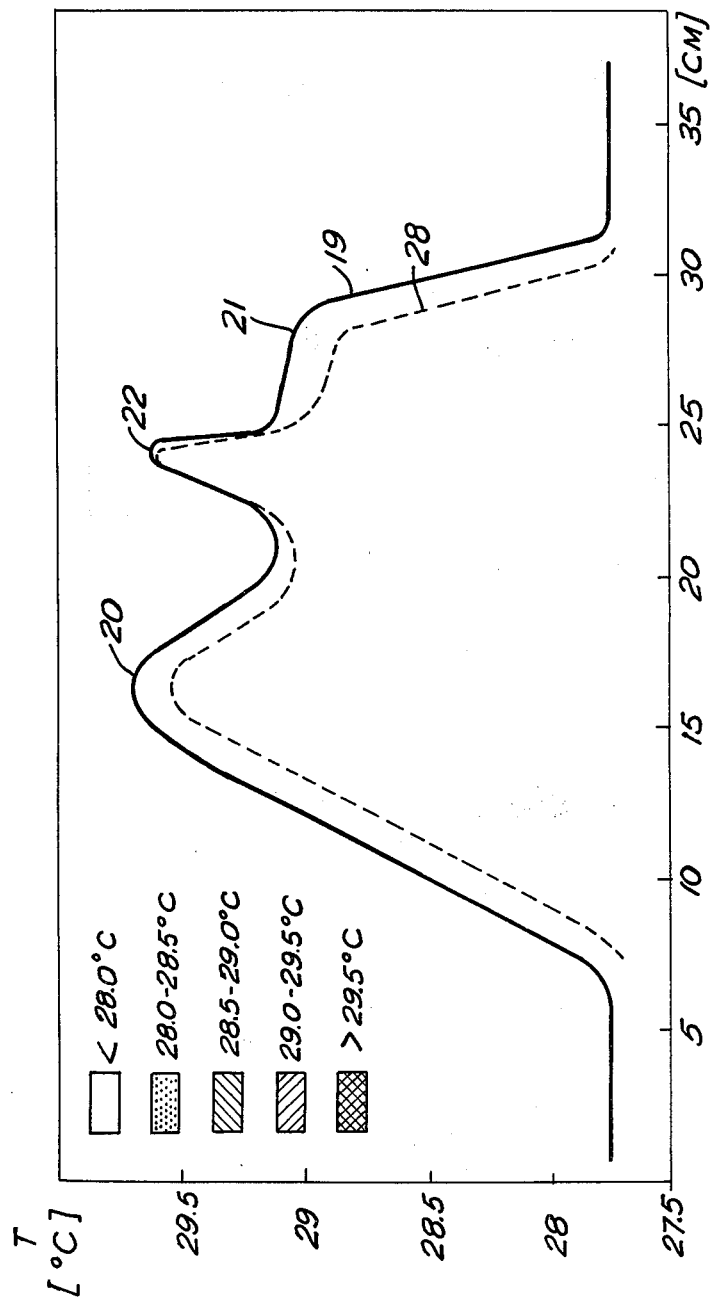
FIG.2
FIG.3

PROCESS FOR THE DIGITIZATION AND DISPLAY OF THERMOGRAPHIC RECORDS

The present invention relates to a process for the digitization and display of thermographic pictures of biological or technical structures in which the temperature values at each image point of a thermogram is digitized and preferably displayed on a viewing screen.

Thermograms or thermographic pictures can be used for a vanity of purposes in order to determine and examine the temperature distributions of biological or technical structures. It is difficult in many cases, however, as for example in a record produced by infra-red photography, to distinguish between locally limited normal temperature distributions and locally limited "abnormal" temperatures.

It is known to those skilled in the art that human tumors (carcinomas) have an "abnormal" temperature behavior which differs from the body shell. In order to detect tumors by means of thermography it has been customary to produce thermographic records of the region to be examined by a thermographic camera and then display these records,—using an analog, digital converter—on a viewing screen. In order to be able to identify tumors more easily, the temperature of the body is reduced by cooling. Since the diseased region of the body follows this change in temperature only to a limited extent the locally differentiated temperature behavior enables conclusions to be drawn with respect to the possible presence of tumors. This method has been used in particular for the detection of breast cancer. The evaluation of the records in the above prior art method visually, i.e. carcinomas were identified on the basis of different gray or color values of the thermographic image.

Due to the considerable uncertainty inherent in this evaluation, thermography has not been accepted in actual practice for the detection of foci of diseases in the human body.

The object of the present invention is to provide a method by which it is possible to recognize abnormal temperature distributions even if they are very small or the corresponding regions differ only slightly in temperature from the adjacent temperatures.

The above object is achieved in accordance with the present invention by calculating the slope of the local change in temperature, i.e. the temperature gradient value for each image point on the basis of the image point temperature and the measured temperature values of its neighboring points and by displaying the local distribution of the temperature gradient for a selected image region. The determination of the temperature gradients for each image point is effected preferably by a process computer whose output signals are displayed as a picture or pictures.

Another embodiment for determining the temperature gradients for each image point includes subjecting the thermographic signals to a Fourier analysis and filtering out, and possibly displaying, only high spatial frequencies.

In principle, it is unimportant by what algorithm the temperature gradient values are ascertained, since computers may be used to compute the desired values.

Minor temperature changes due to the occurrence of dangerous situations, particularly in the medical field, one difficult to recognize in a pictorial display of the temperature values due to their inconspicuousness. However the display of the temperature gradients for each image or for a selected region is far more significant.

It is advantageous to establish in advance staggered threshold values for the temperature gradient values and ascribe color shades to the value ranges thus obtained. The values of the temperature gradients then appear in different colors in the pictorial display so that it is possible to easily recognize danger regions.

It is aso possible to assign the temperature-gradient values a pre-selectable threshold-value which, for instance, delimits the pathological region and reproduces in black and white or other single-color display those measured values which lie below and above the threshold values.

The present invention can be used in various fields of the natural sciences and technology and particularly in the field of medicine for the detection of carcinomas, and particularly breast cancer.

The present invention can also be used for other medical examinations, for instance for the determination of inflammations, rheumatic diseases of the joints, etc. Additionally, aerial photographs can be taken of forests in order to study their water content. In this regard, the thermographic records are evaluated to obtain exact data concerning the distribution of water.

In the technical field the present invention can be used for checking the insulation of buildings, as well as for the thermographic examination of metallic materials.

In principle, the method of the invention can be used wherever a precise temperature course is required, which would otherwise be difficult or impossible to obtain from the thermographic record of the absolute temperature values.

The method of the present invention can also be employed for recording the temperature gradient fields for different body temperatures and comparing them with each other. This comparison can be effected by formation of differences, quotients or other mathematical relationships such as the deviation of linear and/or quadratic extrapolations as well as those of higher order. Since carcinoma-induced structures change differently in the temperature gradient fields with the mean temperature of the surface of the skin than do structures which are based on oncologically non-pathological causes, carcinoma-induced structures can be recognized and displayed by the method described.

Simultaneous with recording the temperature gradient fields, the temperature fields for different body temperatures can also be evaluated and shown alongside or superimposed upon the temperature gradient fields.

The display of the temperature and temperature-gradient fields alongside each other can be effected on two different viewing screens or on a common viewing screen which is, for instance, divided in its center. For a superimposed display a common screen is preferred in which for example, the temperature field, may be depicted in black and white and the other field depicted in either a single color with graded color saturation or in different colors. If only one threshold value which delimits ths pathological region is selected, the display can be effected so that only that pathological region is shown.

It may also be advantageous to display both fields in color, the colors being so selected that the regions to be identified are imparted, by mixing, particularly striking color.

In order to assure particularly simple evaluation it is advantageous to effect the display of the temperature gradient field, or else the superimposed display of this field, on the temperature field in such a manner that the regions to be identified, for instance regions with a larger temperature gradient, blink on and off.

The display of the evaluation of thermographic records can also be effected without the use of viewing screens, i.e. by drawing graphical displays or by numerical values set forth in tabular form.

In the method of the present invention the temperature gradients for each image point are determined by computer. The signals obtained thereby are used, in one embodiment, for the automatic focusing of the thermographic camera. This is possible, by forming the sum of the gradient signals of a relatively large image region and by automatically changing the focus of the camera until this maximum sum is reached. It is also possible to use only the high frequencies in the gradient signal field for the automatic focusing.

The invention will be explained in further detail below with reference to FIGS. 1 to 5 of the accompanying drawings, in which FIG. 1 is a block diagram of one embodiment of an arrangement for the evaluation of thermographic records in accordance with the method of the invention;

FIG. 2 shows the variation of the temperature along a scanning line of the region examined;

FIG. 3 is a presentation of the curve of FIG. 2 in different colors or different shades of gray;

Figure 1:
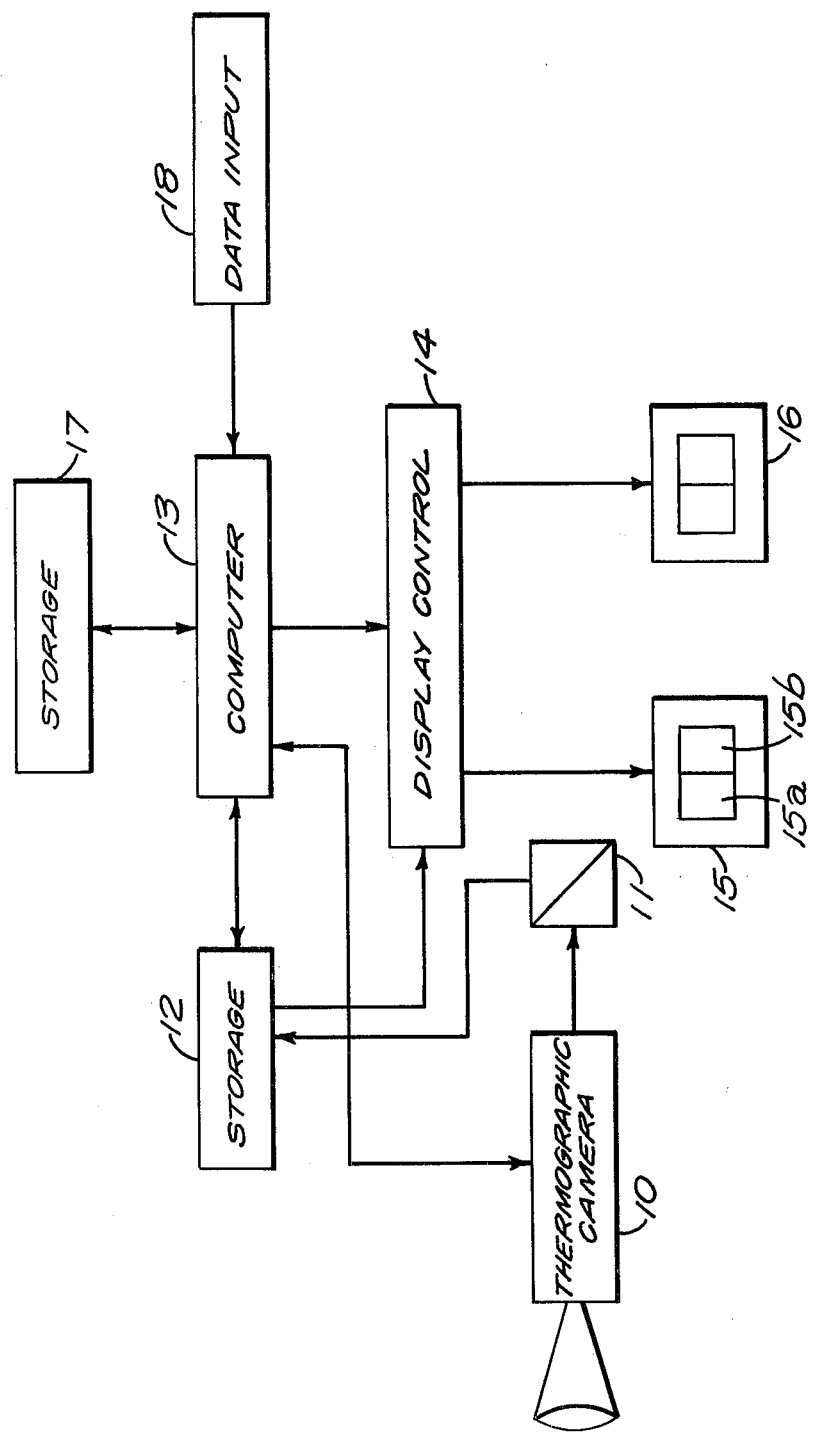

In the arrangement shown in FIG. 1, 10 is a thermographic camera for the taking of thermographic pictures. The signals of the thermograhic camera 10 are fed to analog-digital converter 11 which is connected to it. To the latter is connected a first storage 12 for receiving the digitized image signals.

Storage 12 is in turn connected to a computer 13 which may be a process computer, in which not only permits, an exchange of data but also provides for the return of signals to storage 12 when a calculation operation has been concluded in computer 13.

Storage 12 and computer 13 are each connected to a display control 14 which is connected to monitors 15 and 16 which display the corresponding temperature-gradient values, temperature values, or else the difference or quotient values of temperature gradients or temperatures.

Furthermore, computer 13 is connected, for mutual exchange of data, to a second storage 17 or another computer with connected storage which provides long-term storage of data and receives its data from computer 13. Further data is fed to the latter, via a data input 18, for instance, to another computer, for such control signals as start, stop etc.

In accordance with the present invention the object to be examined is recorded with thermographic camera 10; the values measured are digitized in analog-digital converter 11 and stored in storage 12. For this purpose, the object to be examined is subdivided into a matrix of, for instance, 64×64 image points or 256×256 image points with a distance between image points of, 5 mm and 1.25 mm respectively. Computer 13 calls up the temperature values stored in storage 12, stores them in the storage 17 (large long-term storage) and processes the data called up so as to calculate the temperature gradients for each image point. As a function of the precision of calculation desired, the temperature of four or eight or more adjacent picture points of the screen can be taken into account in the calculation.

The temperature gradient values calculated in this manner are totaled in the computer and the focus of the camera 10 is automatically controlled by the sum signal until the sum signal reaches its maximum and the focusing reaches it stable optimum position.

The temperature gradient values determined after this adjustment are stored in storage 12. Upon completion of the computation computer 13 gives off a signal to storage 12. The latter thereupon feeds the stored signals of the measured temperature values and of the calculated temperature gradient values to display control 14. The latter conducts the signals, to monitor 15, where they are displayed on the screen.

In this connection, the temperature values and the temperature gradient values can either appear on two adjacent viewing-screen regions 15a, 15b of monitor 15 or can be shown superimposed.

In order to readily evaluate the individual thermographic records, more or less finely gradated threshold values are established via data input 18 for the temperature values and temperature gradient values. Computer 13 assigns gray shades or color shades, predetermined in accordance with the pre-established threshold values to the temperature and temperature gradient signals, these shades of gray or color shades then appear on picture screens 15a, 15b or 16.

If it is desired to display temperature values and temperature gradient values alongside each other, one can use as desired gray shades or color shades, the colored presentation of the thermographic pictures being preferable in many cases.

Alternatively or in addition to this critical regions can also be made visible by causing the corresponding points to blink.

One example of an optical display of the ascertained or calculated values is shown in FIGS. 2 to 5. FIG. 2 depicts, curve 19, which represents the measured temperature values along one line of a record recorded with camera 10. This may be a picture line of a thermogram which extends over a 35 cm long strip of skin. The measured temperature values are intended to reproduce, in the region of two maxima 20 and 21 of curve 19, temperatures which result, for instance, from blood vessels which are close to the skin. Between maxima 20 and 21 there is shown another maximum 22 which is due to a relatively small tumor in the body shell.

A presentation of the color or gray-tone values for the temperature regions of the above-explained curve 19 shows, in accordance with FIG. 3, that color regions 23, 24 (or grayshade regions) for the maxima 20 and 22 agree with each other although different identifiable causes are the basis for this curve.

Figure 4:
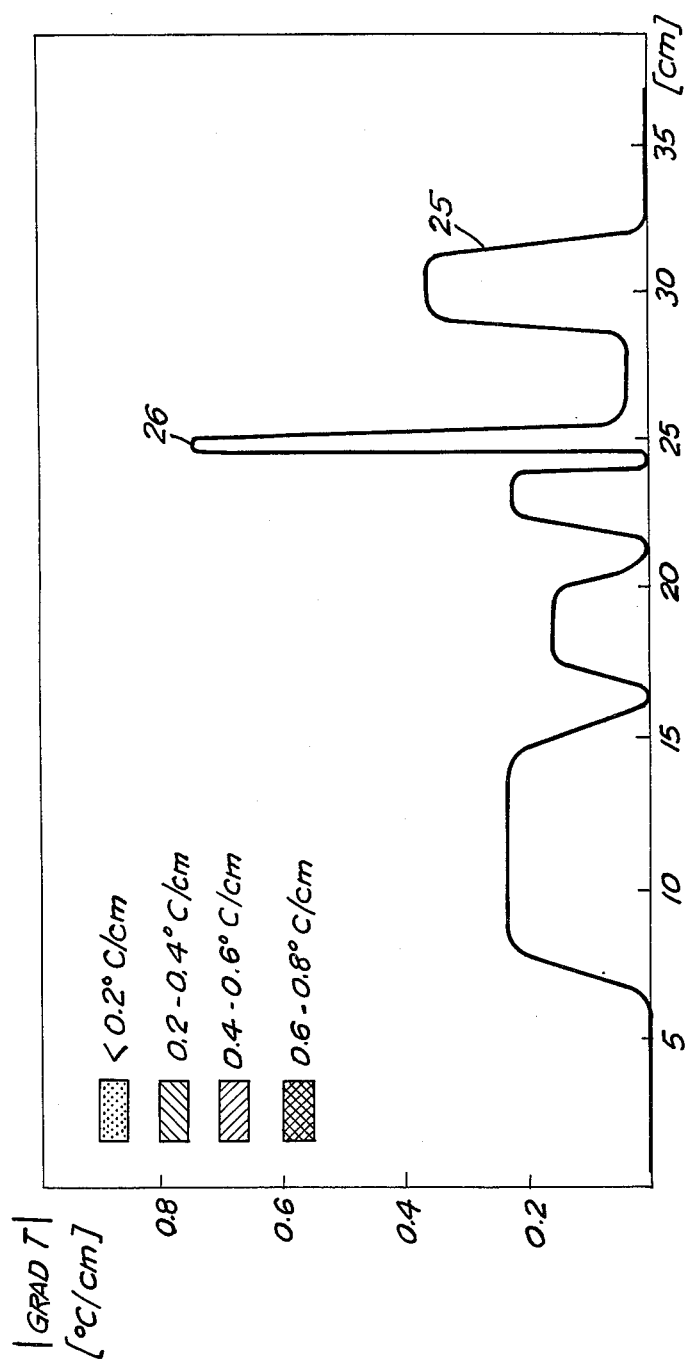
FIG. 4 is a curve which shows the temperature gradient, determined from the curve of FIG. 2, in its variation along the scanning line.
Figure 5:
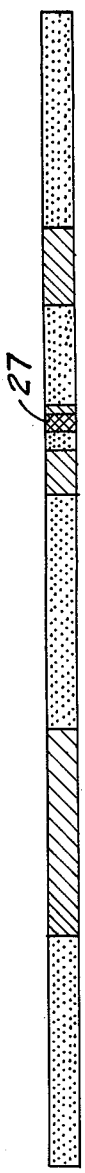
FIG. 5 is a presentation of the curve of FIG. 4 in different colors or different shades of gray.

FIG. 4 shows a curve 25 which represents the temperature gradients corresponding to the temperature values of curve 19 of FIG. 2. As can be noted from curve 25, a maximum 26 is clearly set off as compared with the rest of the curve 25.

If a pictorial representation in accordance with FIG. 3 is recorded for curve 25, that is with color regions associated with the predetermined threshold value regions, it is found that a color region 27 is clearly demarcated from other color regions, which also differ from each other.

In an alternative method for the evaluation of thermograhic records, particularly for the identification of tumors and other regions of different temperature the temperature values of repeated photographs or measurements (but different mean temperatures) are compared with each other. In this method it is taken into consideration that, with different average body temperatures, a tumor maintains substantially a given specific temperature. In FIG. 2, curve 19 measured at a given average temperature is compared with a second curve 28 which corresponds to a lower average temperature of the body surface. The "normally" responding regions of the body shell show here, in all cases, lower temperature values, while in the region of maximum 22 substantially the same temperature values as in curve 19 are noted.

By means of the arrangement in accordance with FIG. 1, the temperature values of different measurements or recordings are compared by computer with each other such that for each image point, the difference or quotient values are determined and displayed on monitor 16. The values of a thermogram which have been previously taken at a different average body temperature can be called forth from storage 17 and compared in computer 13 with the values of the newly recorded thermogram.

This method can be carried out simultaneously with the determination and display of the temperature gradient values, the last-mentioned data being shown simultaneously by means of the other monitor 15. In this way it is possible to compare records which were previously photographed and therefore both local and temporal changes in temperature can be noted. For this purpose storage 17, which is developed as a long-term storage, records data on corresponding data supports.

We claim:

1. A method of digitizing and displaying thermographic records of biological or technical structures in which the temperature values at each image point of a thermogram are digitized, evaluated and displayed, comprising the steps of: calculating the temperature-gradient value for each image point by determining the slope of the local temperature change on the basis of each image point temperature value and the measured temperature values of neighboring image points; and displaying the local distribution of the temperature-gradient values for a selected image region.

2. A method according to claim 1, wherein the temperature values of the image points of the thermogram are displayed simultaneously with the associated temperature-gradient values.

3. A method according to claim 1 or 2, wherein at least one of the group of values selected from the group of temperature values and the temperature-gradient values of the thermogram are classified in several graduated thresholdvalue regions, and optically displayable color shades are associated with the values in said regions.

4. A method according to claim 3, wherein predetermined threshold values are associated with the temperature values and the temperature-gradient values, the temperature values and the temperature-gradient values of the thermograms displayed on a common picture screen, and those regions where the predetermined threshold values of the temperatures and temperature-gradient values exceed the predetermined threshold values being distinguished optically.

5. A method according to claim 1 or 2, wherein a preselected threshold value is associated with at least one of the group of values selected from the group of temperature values and temperature-gradient values such that the measured values lying below and above said threshold value are reproduced in a black-and-white display.

6. A method according to claim 1, wherein the temperature-gradient values are calculated on the basis of the average temperature in selected sections of the image region, and the temperature at each image point.

7. A method according to claim 1 or 6, wherein the temperature-gradient values are used for the automatic focusing of the system for recording the thermographic images.

8. A method for digitizing and displaying thermographic images of biological or technical structures in which the temperature values at each image point of a thermogram are digitized, evaluated and displayed, comprising the steps of: recording the thermographic images at different average temperatures of the structures; calculating the temperature-gradient value for each image point in each of the images by determining the slope of the local temperature change on the basis of each image point temperature value and the measured temperature values of neighboring image points; comparing at least one of the group of values selected from the group of temperature values and temperature-gradient values which correspond to the different temperatures by computer; and displaying the changes in the images.

9. A method according to claim 8, wherein the temperature values determined for a first thermogram and the temperature-gradient values calculated therefrom are displayed on a first picture screen and the difference or quotient values for the temperature values and the temperature-gradient values calculated by comparison of the first thermogram with a second thermogram are displayed on a second picture screen.

10. A method according to claim 2 or 8, wherein the temperature values and the temperature-gradient values of the thermograms are displayed on a common picture screen.

* * * * *